(12) United States Patent
Esfandiari et al.

(10) Patent No.: US 12,427,227 B2
(45) Date of Patent: Sep. 30, 2025

(54) BIOACTIVE SMART SCAFFOLDS FOR REGENERATIVE MEDICINE

(71) Applicant: University of Cincinnati, Cincinnati, OH (US)

(72) Inventors: Leyla Esfandiari, Cincinnati, OH (US); Gregory Harris, Cold Spring, KY (US)

(73) Assignee: University of Cincinnati, Cincinnati, OH (US)

( * ) Notice: Subject to any disclaimer, the term of this patent is extended or adjusted under 35 U.S.C. 154(b) by 0 days.

(21) Appl. No.: 17/768,911

(22) PCT Filed: Oct. 15, 2020

(86) PCT No.: PCT/US2020/055679
§ 371 (c)(1),
(2) Date: Apr. 14, 2022

(87) PCT Pub. No.: WO2021/076694
PCT Pub. Date: Apr. 22, 2021

(65) Prior Publication Data
US 2024/0100223 A1    Mar. 28, 2024

Related U.S. Application Data

(60) Provisional application No. 63/080,521, filed on Sep. 18, 2020, provisional application No. 62/915,035, filed on Oct. 15, 2019.

(51) Int. Cl.
*A61L 27/36* (2006.01)
*A61L 27/38* (2006.01)
(Continued)

(52) U.S. Cl.
CPC ....... *A61L 27/3633* (2013.01); *A61L 27/3878* (2013.01); *A61L 27/50* (2013.01);
(Continued)

(58) Field of Classification Search
CPC .. A61L 27/3633; A61L 27/3878; A61L 27/50; A61L 2400/12; A61L 2430/32; A61N 7/00; A61N 2007/0026
See application file for complete search history.

(56) References Cited

U.S. PATENT DOCUMENTS 9,878,169 B2   1/2018  Hossainy
2002/0042128 A1*  4/2002  Bowlin ............... A61L 27/24
530/382
(Continued)

FOREIGN PATENT DOCUMENTS

CN   106902389 A   6/2017
WO   8806866 A1   9/1988
(Continued)

OTHER PUBLICATIONS

Parrinello, et al., EphB Signaling Directs Peripheral Nerve Regeneration through Sox2-Dependent Schwann Cell Sorting, Cell, vol. 143, pp. 145-155, Oct. 1, 2010. (Year: 2010).*
(Continued)

*Primary Examiner* — Alexei Bykhovski
(74) *Attorney, Agent, or Firm* — DINSMORE & SHOHL LLP

(57) ABSTRACT

Provided herein are implantable biomaterials for promoting regeneration of an injured biological tissue, the biomaterials including piezoelectric materials and an extracellular matrix specific to the injured biological tissue, wherein the piezoelectric materials and the extracellular matrix are electrospun together to provide tissue-specific bioactive piezoelectric nanofiber scaffolds. Also provided herein are methods of fabricating a tissue-specific bioactive piezoelectric nanofiber scaffold and methods of promoting regeneration of injured biological tissue by implanting the disclosed bioactive piezoelectric scaffolds.

23 Claims, 8 Drawing Sheets

(51) Int. Cl.
*A61L 27/50* (2006.01)
*A61N 7/00* (2006.01)

(52) U.S. Cl.
CPC ............ *A61N 7/00* (2013.01); *A61L 2400/12* (2013.01); *A61L 2430/32* (2013.01); *A61N 2007/0026* (2013.01)

(56) References Cited

U.S. PATENT DOCUMENTS

| | | | |
|---|---|---|---|
| 2008/0208358 A1 | 8/2008 | Bellamkonda et al. | |
| 2013/0052254 A1* | 2/2013 | Arinzeh | C12N 5/0618 424/443 |
| 2019/0142998 A1 | 5/2019 | Machluf et al. | |
| 2020/0276018 A1 | 9/2020 | Nguyen et al. | |

FOREIGN PATENT DOCUMENTS

| | | | |
|---|---|---|---|
| WO | 2007149936 | A2 | 12/2007 |
| WO | WO 2007149936 | * | 12/2007 |
| WO | 2012014205 | A1 | 2/2012 |
| WO | 2018187407 | A1 | 10/2018 |

OTHER PUBLICATIONS

Ahn (Relevance of Collagen Piezoelectricity To "Wolff's Law": a Critical Review, Med Eng Phys. Sep. 2009 ; 31(7): 733-741). (Year: 2009).*
EP Extended European Search Report dated Oct. 9, 2023 pertaining to EP application No. 20877363.0 filed May 5, 2022, pp. 1-10.
Wu, S. et al. "Aligned fibrous PVDF-TrFE scaffolds with Schwann cells support neurite extension and myelination in vitro" Journal of Neural Engineering, Institute of Physics Publishing, Jul. 18, 2018, pp. 1-11, vol. 15.
International Search Report and Written Opinion mailed on Jan. 4, 2021 in reference to co-pending Application No. PCT/US2020/055679 filed Oct. 15, 2020.
Parrinello, et al., "EphB Signaling Directs Peripheral Nerve Regeneration through Sox2-Dependent Schwann Cell Sorting", Cell, vol. 143, pp. 145-155, Oct. 1, 2010.
Harris, et al., "Cell-derived decellularized extracellular matrices", Methods Cell Biol., vol. 143, pp. 97-114, 2018.
EP Communication pursuant to Article 94(3) EPC dated Apr. 3, 2025 pertaining to EP application No. 20877363.0 filed May 5, 2022, pp. 1-7.

* cited by examiner

BIOACTIVE SMART SCAFFOLDS FOR REGENERATIVE MEDICINE

CROSS-REFERENCE TO RELATED APPLICATIONS

This application is a § 371 National Stage Application of International Application Serial No. PCT/US2020/055679, filed Oct. 15, 2020, and claims priority to U.S. Provisional Application Ser. No. 62/915,035, filed Oct. 15, 2019, and U.S. Provisional Application Ser. No. 63/080,521, filed Sep. 18, 2020, each of which is incorporated herein by reference in its entirety.

TECHNICAL FIELD

The present disclosure relates to the field of biomaterials and their fabrication and use. More specifically, the present disclosure relates to biocompatible piezoelectric biomaterials and their methods of fabrication and use in regenerative medicine.

BACKGROUND

Peripheral nerves (PNs) are the direct connection from the central nervous system to the rest of the body and are easily impaired through injury. Injuries to PNs can occur from any traumatic instance, such as car accidents, sports injuries, or as a result of surgery (e.g., tumor removal). Injuries to peripheral nerves are the second most frequent cause of permanent disability following combat wounds in soldiers. In recent conflicts in Afghanistan and Iraq, the majority of the permanent disability cases were due to musculoskeletal wounds and nerve injuries. Apart from battlefield injuries, PN injuries impact 1.4 million Americans each year, with many millions of people currently living with the effects of traumatic nerve injury.

PN dysfunction can affect patients in multiple ways, including loss of function, chronic neuropathic pain, and disability. To restore function following nerve damage, neurons must extend new axons, cross the lesion site, and find and innervate the appropriate distal targets. However, recovery after severe lesions, such as a complete transection, is limited by factors such as deficient or non-specific nerve outgrowth, insufficient methods of recreating and repairing lost nerve segments, and neuropathic pain disorders.

Regenerative medicine applies tissue engineering and life science principles to promote healing and/or regeneration of injured or lost tissue. Mao, et al., *Regenerative medicine: Current therapies and future directions, PNAS* 112(47): 14452-59 (2015). Approaches to regenerative medicine include, for example, biologics for the delivery of therapeutic cells, cell-based medical devices, and biopharmaceuticals.

Currently, the standard of care for treating peripheral nerve injuries is use of an autograft to bridge the injury. However, inconsistent success rates have been observed, availability of donor nerves is limited, mismatch of nerve size between donor and recipient nerves is frequently problematic, and the process itself may require multiple surgeries. While allografts have shown promise for the replacement of autografts, they introduce the risk of immuno- and disease-related complications. Artificial nerve conduits have been explored, but are plagued with issues such as matching substrate flexibility with cell/tissue flexibility, porosity, and the ability to be self-powered to promote neuronal regeneration across defect gaps.

Biomaterials, such as 3D polymer scaffolds, have been developed for use in promoting tissue regeneration. However, managing the immune system response to implanted biomaterials continues to present a significant challenge. Implanted biomaterials may elicit an undesirable immune response, such as tissue rejection or inflammation, or may result in immune clearance of bioactive cells, thereby limiting treatment efficacy.

A need exists for improved biomaterials for promoting regeneration and healing of injured biological tissues.

SUMMARY

Accordingly, provided herein are bioactive, piezoelectric nanofiber scaffolds having applications in regenerative medicine. The presently disclosed biomaterials employ tissue-specific components and engineered piezoelectric nanofiber scaffolds to drive tissue regeneration, and in particular nerve regeneration, across traumatic injury gaps, while minimizing the immune response to the bioactive scaffold.

In one embodiment, an implantable biomaterial for promoting regeneration of a biological tissue is provided, the biomaterial comprising: a piezoelectric material; and an extracellular matrix specific to the injured biological tissue, wherein the piezoelectric material and the extracellular matrix are electrospun together to provide a tissue-specific bioactive piezoelectric nanofiber scaffold.

In another embodiment, a method for fabricating a biomaterial for regeneration of a biological tissue is provided, the method comprising: electrospinning a piezoelectric material together with an extracellular matrix specific to the injured biological tissue to provide a tissue-specific bioactive piezoelectric nanofiber scaffold.

In another embodiment, a method of promoting regeneration of injured biological tissue in a patient in need thereof is provided, the method comprising: providing a tissue-specific bioactive piezoelectric nanofiber scaffold comprising a piezoelectric material and an extracellular matrix specific to the injured biological tissue of the patient, wherein the piezoelectric material and the extracellular matrix are electrospun together to form nanofibers; and implanting the tissue-specific bioactive piezoelectric nanofiber scaffold at the site of the injured biological tissue of the patient, wherein the tissue-specific bioactive piezoelectric nanofiber scaffold delivers one or more stimuli to the site of the injured biological tissue that promote regeneration of the injured biological tissue.

These and other objects, features, embodiments, and advantages will become apparent to those of ordinary skill in the art from a reading of the following detailed description and the appended claims.

BRIEF DESCRIPTION OF THE DRAWINGS

The details of embodiments of the presently-disclosed subject matter are set forth in this document. Modifications to embodiments described in this document, and other embodiments, will be evident to those of ordinary skill in the art after a study of the information provided in this document.

DETAILED DESCRIPTION

Figure 1:
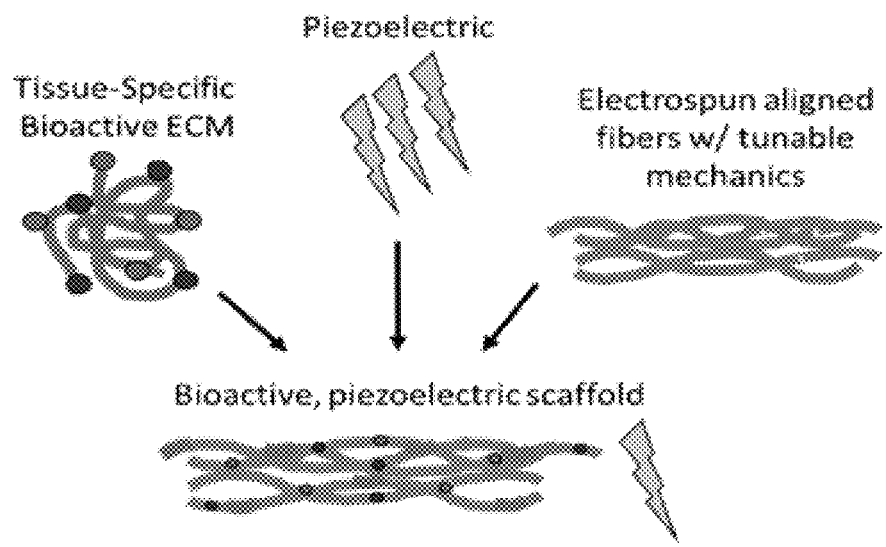
FIG. 1 is a graphic depiction of an embodiment of a bioactive, piezoelectric scaffold according to the present disclosure.

The details of one or more embodiments of the presently-disclosed subject matter are set forth in this document. Modifications to embodiments described in this document, and other embodiments, will be evident to those of ordinary skill in the art after a study of the information provided in this document.

While the following terms are believed to be well understood in the art, definitions are set forth to facilitate explanation of the presently-disclosed subject matter. Unless defined otherwise, all technical and scientific terms used herein have the same meaning as commonly understood by one of ordinary skill in the art to which the presently-disclosed subject matter belongs.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

As used in this specification and the appended claims, the singular forms "a," "an" and "the" include plural references unless the content clearly dictates otherwise.

As used herein, the term "patient" refers to any mammalian subject, including humans, non-human primates, pigs, dogs, rats, mice, and the like. In a specific embodiment, the patient is a human patient.

"Biomaterial," as used herein, refers to a substance that is engineered or synthesized to interact with biological systems for a therapeutic or diagnostic purpose. Biomaterials contact living cells, tissues, organisms, or microorganisms and such contact between biomaterial and biological cells or tissue may be exploited to effect a particular outcome. A bioactive biomaterial is a biomaterial that induces a physiological response supportive of the biomaterial's function and performance.

"Nanofiber," as used herein, refers to a fiber having a diameter in the nanometer range. In embodiments, the nanofibers disclosed herein comprise piezoelectric materials, such as polymers, and in particular, piezoelectric polymers. In embodiments, the nanofibers disclosed herein comprise extracellular matrix (ECM), including tissue-specific ECM. Such nanofibers may be produced by a variety of techniques. In particular embodiments, the disclosed nanofibers are produced via electrospinning.

"Electrospinning" and "electrospun," as used herein, refer to a process for transforming a composition, such as a polymer composition, to a nanofiber via application of a high voltage electric field. Instruments necessary for electrospinning include a high voltage supplier, a capillary tube with a pipette or needle with a small diameter, and a metal collecting screen. One electrode is placed into the polymer solution and the other electrode is attached to the collector. An electric field is applied to the end of the capillary tube that contains the polymer solution held by its surface tension and forms a charge on the surface of the liquid. As the intensity of the electric field increases, the hemispherical surface of the fluid at the tip of the capillary tube elongates to form a conical shape known as the Taylor cone. A critical value is attained upon further increase in the electric field in which the repulsive electrostatic force overcomes the surface tension and the charged jet of fluid is ejected from the tip of the Taylor cone. The discharged polymer solution jet is unstable and elongates as a result, allowing the jet to become long and thin. Charged polymer fiber solidifies with solvent evaporation. Randomly-oriented nanofibers are collected on the collector. Nanofibers can also be collected in a highly aligned fashion by using specialized collectors, such as a rotating drum or mandrel, metal frame, or a two-parallel plates system.

"Aligned," as used herein, refers to electrospun nanofibers deposited in a substantially uniaxial conformation. Such aligned or substantially aligned fibers may be produced, for example, by electrospinning with the use of a rotating drum or mandrel collector. The topographic features of aligned nanofiber scaffolds create contact guidance for growing cells. For example, an aligned nanofiber scaffold fabricated as disclosed herein facilitates directional growth and alignment of cells present in the microenvironment of a peripheral nerve injury.

"Extracellular matrix" and "ECM," as used herein, refer to the network of extracellular macromolecules that provide structural and biochemical support to cells in a biological environment. ECM is present in all tissues of the body and comprises an organized network that regulates cell behavior and influences development. ECM may comprise, for example, collagen, elastin, fibronectin, laminin, enzymes, growth factors, glycoproteins, and the like. The composition of ECM varies depending on the composition of the particular biological microenvironment of the localized cells/tissue from which the ECM is obtained. In embodiments, ECM is obtained by decellularizing and, optionally, lyophilizing one or more cells native to a particular biological microenvironment. In embodiments, such microenvironment may include that of a peripheral nerve cell.

Figure 3:
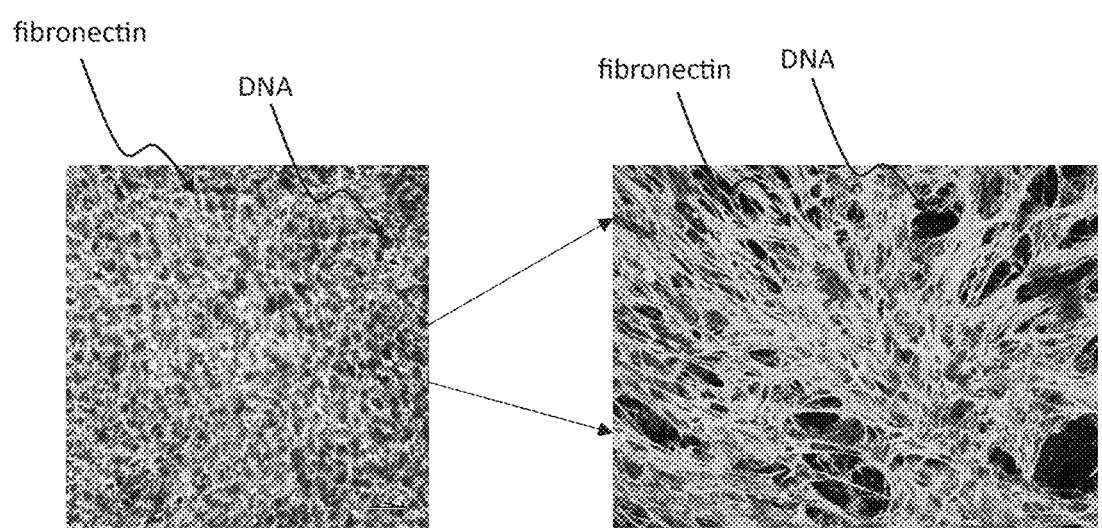
FIG. 3 is a set of images of extracellular matrix at different magnifications comprising imaged fibronectin and laminin.

In embodiments, the ECM employed in the disclosed piezoelectric biomaterials is a tissue-specific ECM. Tissue-specific ECM provides a microenvironment that supports cell growth and differentiation. That is, the ECM is selected to approximate the ECM of the native tissue microenvironment of the implant region of the patient. For example, with respect to the peripheral nerve microenvironment, ECM may be obtained from a co-culture of cells native to the peripheral nerve microenvironment. In a very specific embodiment, the ECM is obtained from a co-culture of fibroblasts and Schwann cells, as described herein below. The ECM may comprise fibronectin, a cell adhesive and bioactive matrix protein, and laminin, a key component of basal lamina of the nerve that functions as a cell adhesive and bioactive. FIG. 3 depicts microscopic images at different magnifications of an ECM typical of a nerve microenvironment. However, it should be understood that the instant disclosed piezoelectric biomaterials have application in a broad spectrum of cells and tissues, and that the ECM may be isolated from our selected to correspond to the ECM of any of such cell and tissue microenvironments.

Piezoelectric materials are materials that generate an electric charge in response to an applied mechanical stress. Piezoelectric materials enhance tissue growth by providing an electrically active microenvironment, without the need for external power sources for electrical stimulation. Biological electric fields in host tissues play significant roles in functions such as neuromuscular activity, glandular secretion, cell membrane function, and tissue growth and repair. See Zhang, et al., *Advanced smart biomaterials and constructs for hard tissue engineering and regeneration*, Bone Research 6, article 31 (2018).

In general, "smart" (or intelligent) biomaterials and constructs refer to biomaterials and constructs that: (1) possess instructive/inductive or triggering/stimulating effects on cells and tissues by engineering the material's responsiveness to internal or external stimuli, such as pH, temperature, ionic strength, or magnetism, to promote damaged tissue repair and regeneration; or (2) have intelligently tailored individual properties and controlled functions to actively participate in tissue regeneration.

Disclosed herein are smart piezoelectric biomaterials comprising an electroactive scaffold for enhancing or facilitating growth and/or repair of a biological cell and/or a tissue, particularly an injured tissue. The piezoelectric biomaterial acts as a highly sensitive mechanoelectrical transducer that generates a charge in response to minute vibrational forces. In embodiments, the piezoelectric biomaterials comprise a three-dimensional scaffold of nanofibers of piezoelectric polymers used as an implantable scaffolding for the growth of cells. The piezoelectric scaffolds, which demonstrate electrical activity in response to minute mechanical deformation, allow the achievement of local electric fields characteristic of the natural extracellular matrix observed during development and regeneration or repair of cells and tissues. The incorporation of tissue-specific ECM into the electrospun nanofibers further promotes cellular growth and regeneration, while simultaneously minimizing immune responses to the implanted biomaterial. See FIG. 1. Tissue specific ECM provides a relevant protein and growth factor composition which improves cell growth and alignment in the injury region.

In one embodiment, an implantable biomaterial for promoting regeneration of a biological tissue, including an injured biological tissue, is provided, the biomaterial comprising: a piezoelectric material; and an extracellular matrix (ECM) specific to the injured biological tissue, wherein the piezoelectric material and the extracellular matrix are electrospun together to provide a tissue-specific bioactive piezoelectric scaffold.

In embodiments, the piezoelectric material comprises a material selected from the group consisting of polyvinylidene fluoride-trifluoroethylene (PVDF-TrFE), barium titanate (BT), sodium potassium niobate (KNN), boron nitride (BN), zinc oxide (ZnO), poly-L-lactic acid (PLLA), PVDF copolymers, polyhydroxybutyrate (PHB) copolymers, polylactic acid (PLA), collagen, and combinations thereof. Additional suitable piezoelectric materials are disclosed, for example, Kapat, et al., *Piezoelectric Nano-Biomaterials for Biomedicine and Tissue Regeneration*, Advanced Functional Materials, DOI: 10.1002/adfm.201909045 (2020). Selection of a suitable piezoelectric material for use in the instant biomaterials and methods will depend on the specific tissue to be treated and the desired properties of the scaffold, and is within the purview of the ordinary skilled artisan. In a specific embodiment, the piezoelectric material is PVDF-TrFE polymer.

Figure 9:
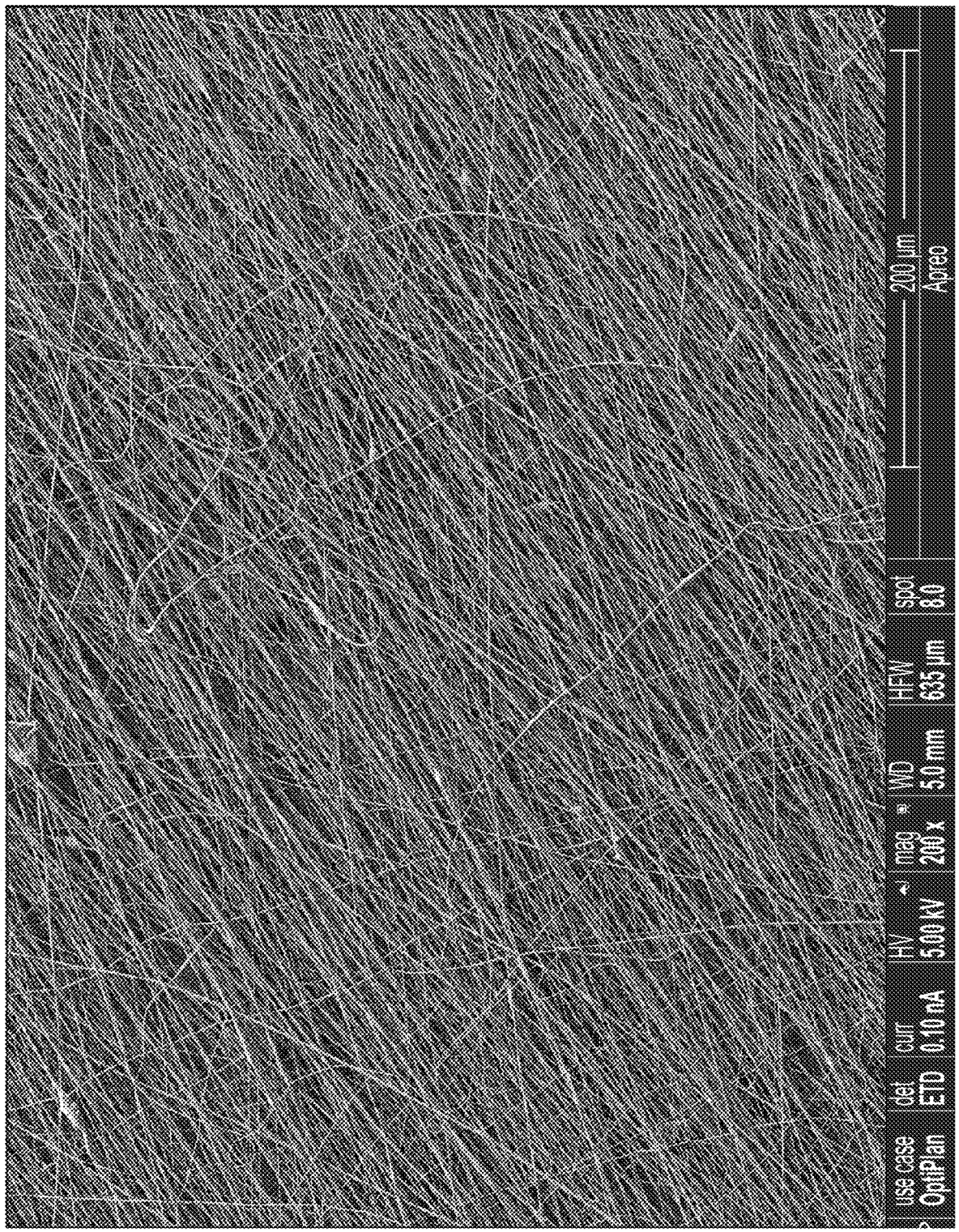
FIG. 9 is a SEM image of PVDF-TrFE nanofibers at 2000× magnification, with a white arrow indicating direction of nanofiber alignment.
Figure 10:
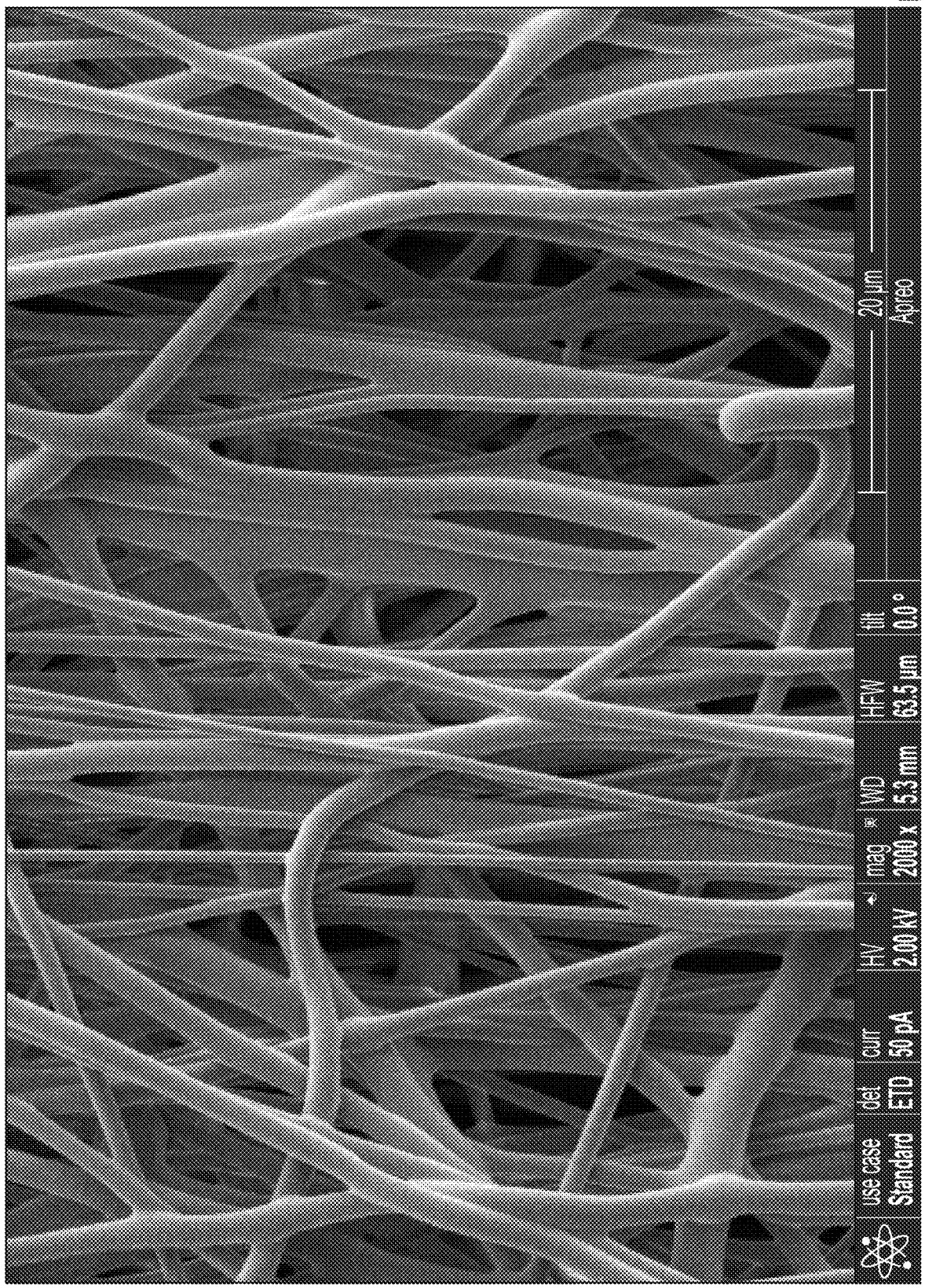
FIG. 10 is a SEM image of PVDF-TrFE nanofibers at 2000× magnification.

In embodiments, the electrospun piezoelectric nanofibers are substantially uniaxially aligned. By "substantially" is understood the nanofibers are at least 50%, at least 60%, at least 70%, at least 80%, at least 90%, at least 95%, at least 99%, or about 100% uniaxially aligned. In embodiments, the alignment of nanofibers advantageously promotes cellular growth along the direction of the aligned fibers. In a specific embodiment, such nanofiber alignment promotes growth and/or regeneration of nerve cells directionally along the nanofibers, and optionally across a peripheral nerve injury or gap. Exemplary ECM-free electrospun piezoelectric nanofibers are depicted in FIG. 9 (PVDF-TrFE spun for 2 hours, viewed at 200× magnification) and FIG. 10 (PVDF-TrFE spun for 2 hours, viewed at 2,000× magnification).

In embodiments, the ECM for use in the disclosed biomaterial scaffolds is derived from cells native to a microenvironment of the injured biological tissue. For example, in embodiments, the injured biological tissue is selected from nerve, bone, skin, cartilage, tendons, ligaments, muscle, heart, and combinations thereof. In a very specific embodiment, the injured biological tissue comprises nerve tissue. In another specific embodiment, the biological tissue comprises peripheral nerve tissue and the extracellular matrix is derived from a co-culture of cells specific to the microenvironment of peripheral nerve tissue, including for example Schwann cells and fibroblasts. In a more specific embodiment, the ratio of fibroblasts to Schwann cells in the co-culture is about 1:1, 1:2, 1:3, 1:4, 1:5, 1:6, 1:7, 1:8, 1:8, or 1:10. In another specific embodiment, the ratio of fibroblasts to Schwann cells in the co-culture ranges from about 1:1 to about 1:5. Such an exemplary nerve tissue-specific ECM comprises, for example, fibronectin and/or laminin, which are native components of the nerve ECM. In embodiments, the cells native to the microenvironment of the injured biological tissue from which the ECM is isolated may be allogeneic or autologous to the patient.

Method of deriving ECM from tissue and cell cultures are well known in the art. Exemplary protocols are found, for example, in Harris, et al., *Nerve Guidance by a Decellularized Fibroblast Extracellular Matrix, Matrix Biology* 60-61: 176-89 (2017); and Harris, et al., *Chapter 5: Cell-derived decellularized extracellular matrices, Methods in Extracellular Matrix Biology*, Robert. P. Mecham, Ed., vol. 143: 97-114 (2018). In embodiments, ECM is derived using a lysis-based protocol. In a specific embodiment, cells are serially washed with phosphate buffered saline (PBS), a wash buffer (100 mM $Na_2HPO_4$, pH 9.6, 2 mM $MgCl_2$, 2 mM EGTA), and then treated with a lysis buffer (8 mM $Na_2HPO_4$, pH 9.6, 1% NP-40) and incubated for 15 minutes at 37° C. Lysis buffer is removed and replaced with fresh lysis buffer and incubation is continued for approximately 40-100 min. Matrices are then washed with a second wash buffer (300 mM KCl, 10 mM $Na_2HPO_4$, pH 7.5) and deionized water until lysate is completely removed, leaving behind the ECM. ECM may be stored in PBS and lyophilized for use in the disclosed methods.

In embodiments, a method for fabricating a biomaterial for regeneration of a biological tissue, including an injured biological tissue, is provided, the method comprising: electrospinning a piezoelectric material together with an extracellular matrix specific to the biological tissue to provide a tissue-specific bioactive piezoelectric nanofiber scaffold.

In embodiments, the piezoelectric material is selected from the group consisting of polyvinylidene fluoride-trifluoroethylene (PVDF-TrFE), barium titanate (BT), sodium potassium niobate (KNN), boron nitride (BN), zinc oxide (ZnO), poly-L-lactic acid (PLLA), PVDF copolymers, polyhydroxybutyrate (PHB) copolymers, polylactic acid (PLA), collagen, and combinations thereof. Additional suitable piezoelectric materials are disclosed, for example, Kapat, et al., *Piezoelectric Nano-Biomaterials for Biomedicine and Tissue Regeneration, Advanced Functional Materials*, DOI: 10.1002/adfm.201909045 (2020). In embodiments, the electrospun piezoelectric nanofibers are substantially uniaxially aligned. In a specific embodiment, the piezoelectric material is PVDF-TrFE polymer.

Concentration of PVDF-TrFE in the hybrid composition for electrospinning may range, for example from about 10% to about 25% (w/v) PVDF-TrFE in (6:4) dimethylformamide (DMF)-acetone. In a more specific embodiment, the concentration of PVDF-TrFE is about 20% (w/v) in (6:4) DMF-acetone. The concentration of PVDF-TrFE and solvent are selected to maximize the highest beta phase of the scaffold, thereby promoting piezoelectric capacity of the polymer.

ECM and piezoelectric materials are electrospun together through a variety of techniques. For example, in embodiments, lyophilized tissue-specific ECM is dissolved or suspended in the piezoelectric polymer solution to provide a hybrid composition for electrospinning. In a specific embodiment, milled, lyophilized ECM is added to 20% w/v PVDF-TrFE in (6:4) DMF-acetone solution for a final ECM concentration of approximately 0.05% to 0.1% w/v. The solution is mixed until the lyophilized ECM is dissolved or substantially homogenously dispersed. Electrospinning can then be carried out according to protocols, with sufficient attention paid to ensure that ECM particles do not aggregate within the dispensing syringe and impact flow and deposition of nanofibers.

Alternatively, ECM may be solubilized through use of an immersed pre-hydrogel solution, as described by Freytes et al., *Preparation and rheological characterization of a gel form of the porcine urinary bladder matrix, Biomaterials* 29(11): 1630-07 (2008). Briefly, pepsin and ECM powders are added at 0.1% and 1% concentrations, respectively, to a solution of 0.01 M HCl. Digestion proceeds for at least 48 hours at room temperature, with the understanding that changes in digestion time may affect resulting biomaterial properties. The resulting viscous solution is then immersed within the 20% w/v PVDF-TrFE in (6:4) DMF-acetone solution and electrospun accordingly. Alternative methods of solubilizing ECM are also available, where urea or acetic acid are used in place of HCl, and in conjunction with salt buffer solutions, for extraction and digestion. See, for example, Lin, et al., *Influence of decellularized matrix derived from human mesenchymal stem cells on their proliferation, migration and multi-lineage differentiation potential, Biomaterials* 33(18): 4480-08 (2012); Saldin, et al., *Extracellular matrix hydrogels from decellularized tissues: structure and function, Acta Biomater* 49: 1-15 (2017).

Once the hybrid composition is prepared (i.e., a composition comprising one or more piezoelectric materials and ECM dissolved or dispersed therein), electrospinning of the hybrid composition is carried out according to standard protocols. See, for example, Xue, et al., *Electrospinning and Electrospun Nanofibers: Methods, Materials, and Applications, Chem. Rev.* 119(8): 5298-5415 (2019); Orkwis, et al., *Development of a Piezoelectric PVDF-TrFE Fibrous Scaffold to Guide Cell Adhesion, Proliferation, and Alignment, Macromolecular Bioscience* 20(9); DOI: 10.1002/mabi.202000197 (2020), each of which is incorporated herein by reference in its entirety. The skilled artisan will appreciate that the electrospinning process may be modified to tune the mechanics of the desired biomaterial scaffolds. For example, selection of the solvent, concentration of piezoelectric material, and length of spin time may be modified to optimize fiber diameter and scaffold porosity. Generally, longer spin times (e.g., about 3 hours) will contribute to lower porosity and higher diameter fibers.

Also provided herein is a method of promoting regeneration of injured biological tissue in a patient in need thereof, the method comprising: providing a tissue-specific bioactive piezoelectric nanofiber scaffold comprising a piezoelectric material and an extracellular matrix specific to the injured biological tissue of the patient, wherein the piezoelectric material and the extracellular matrix are electrospun together to form nanofibers; and implanting the tissue-specific bioactive piezoelectric nanofiber scaffold at the site of the injured biological tissue of the patient, wherein the tissue-specific bioactive piezoelectric nanofiber scaffold delivers one or more stimuli to the site of the injured biological tissue that promote regeneration of the injured biological tissue.

In embodiments, the one or more stimuli are selected from an electrical stimulus, a physical stimulus, and a chemical stimulus. For example, physical and electrical stimuli may be provided by deformation of the piezoelectric scaffold, while the chemical stimulus may be provided by the integrated tissue-specific ECM.

In another embodiment, the method further comprises applying ultrasound stimulation locally to an implantation region of the patient to selectively stimulate the bioactive piezoelectric scaffold implanted in the patient. In a specific embodiment, the ultrasound stimulation comprises minimally-invasive low intensity ultrasound stimulation, as is typically employed in rehabilitative therapies.

Ultrasound stimulation has previously been shown to improve neural cell and tissue regeneration. Moreover, non-neural tissues such as bone, muscle, heart, and traumatized injured tissues that require wound dressings may also obtain a benefit from ultrasound therapy. Thus, ultrasound stimulation to a local implantation region of a patient serves to both selectively stimulate the implanted bioactive piezoelectric scaffold, as well as deliver an additional therapeutic benefit to promote tissue healing and regeneration.

EXAMPLES

The following examples are given by way of illustration are not intended to limit the scope of the disclosure.

Example 1. Preparation and Analysis of Tissue-Specific Extracellular Matrix

Figure 4:
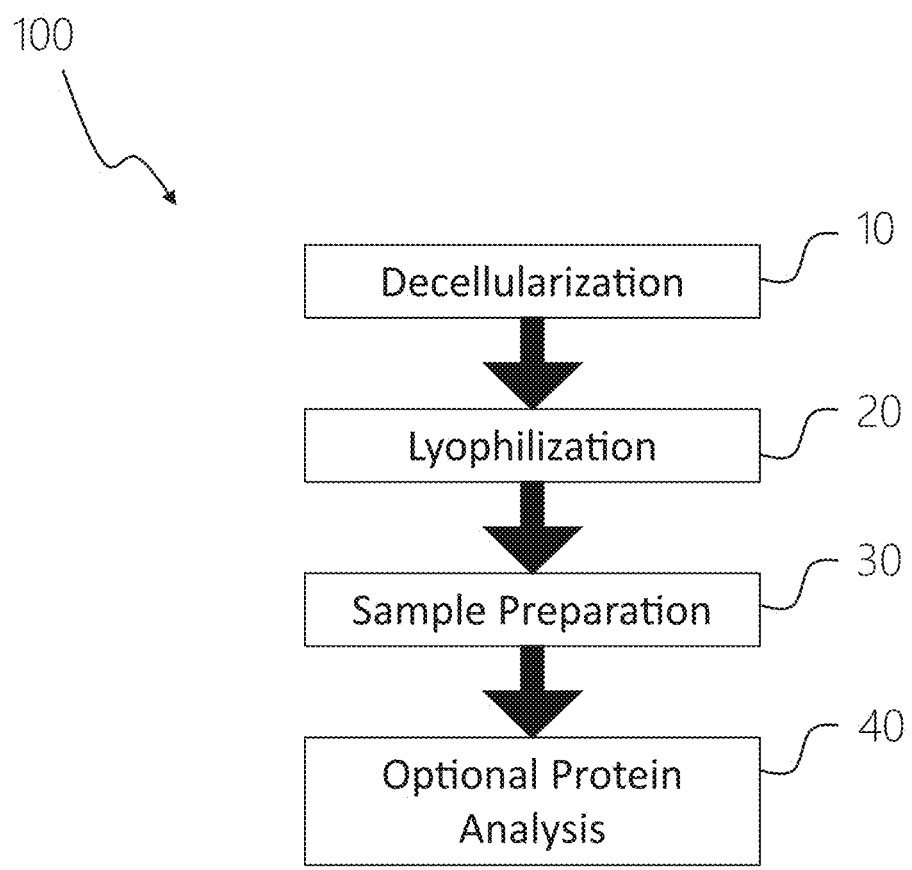
FIG. 4 is a flow chart showing a process for isolating and preparing tissue-specific extracellular matrix according to an embodiment of the present disclosure.

FIG. 4 sets forth a method 100 of preparing tissue-specific ECM that comprises decellularization 10, lyophilization 20, sample preparation 30, and optional protein analysis 40.

For decellularization, cultures of 3T3 fibroblasts and RT4-D6P2T Schwann cells (SCs) typical of the peripheral nerve injury microenvironment were seeded in regenerative media (DMEM:F12+L-glutamine, 10% fetal bovine serum, 1% antibiotics, 10 ng/ml neuregulin, and 5 ng/ml TGFβ1) as follows: 3T3 fibroblasts only, SCs only, and a fibroblast:SC ratio of 1:1, 1:3, and 1:5, at a density of about 18,000 cells/cm$^2$. The cells were supplemented with 50 μg/ml ascorbic acid every 48 hours On day 7, 4 days past confluency, decellularization was carried out using established protocols.

ECM is derived using a lysis-based protocol. Cells were washed with phosphate buffered saline (PBS), a wash buffer (100 mM $Na_2HPO_4$, pH 9.6, 2 mM $MgCl_2$, 2 mM EGTA), and then treated with a lysis buffer (8 mM $Na_2HPO_4$, pH 9.6, 1% NP-40) and incubated for 15 minutes at 37° C. Lysis buffer was removed and replaced with fresh lysis buffer and incubation is continued for approximately 40-100 min. Matrices were then washed with a second wash buffer (300 mM KCl, 10 mM $Na_2HPO_4$, pH 7.5) and deionized water until lysate was completely removed, leaving behind the ECM. ECM samples were stored in PBS until lyophilization (preferably, within 4 days).

Lyophilization was carried out by storing the sample at −4° C. for 24 hours, freezing the sample at −20° C. overnight, freezing the sample at −80° C. for 2-4 hours, and then lyophilizing according to standard protocols (Freezone 1L Benchtop Freeze Dry System).

The ECM sample was prepared by suspending the lyophilized product in Laemilli buffer, vortexing, boiling for 10 min at 96° C., cooling, centrifuging, and extracting the supernatant protein composition.

Figure 5:
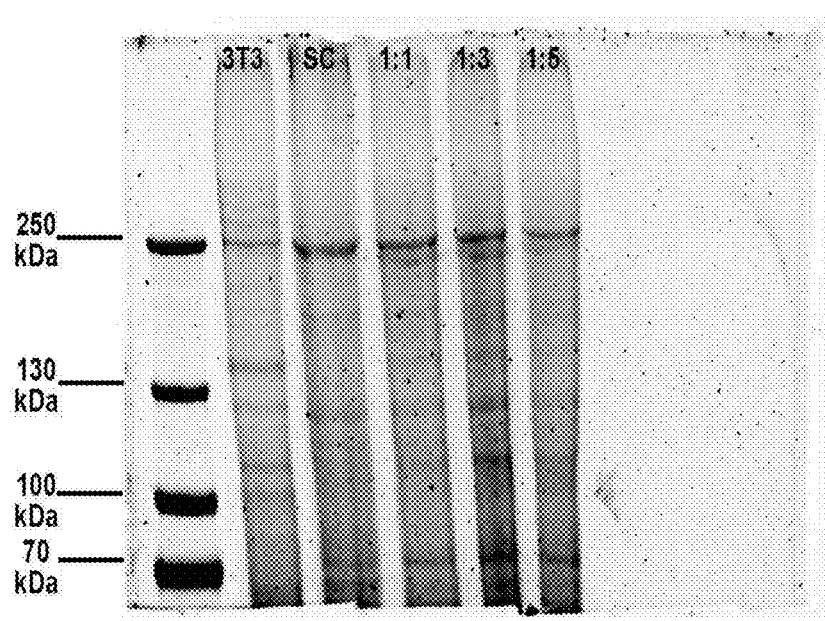
FIG. 5 is an image of a Coomassie stained SDS-PAGE gel for quantifying proteins in decellularized 3T3 fibroblast cells, Schwann cells, and co-cultures of 3T3 and SC cells in ratios of 1:1, 1:3, and 1:5 respectively. Gel wells were loaded with 12.5 µg decellularized ECM/well. Proteins were quantified using NanoDrop A280 (ThermoFisher).

Protein concentration was quantified via mass spectrometry (NanoDrop A280, Thermofisher). Proteins were denatured with DTT, separated via SDS-PAGE (gels were loaded with 12.5 μg decellularized ECM/well), and imaged with Coomassie blue stain, with results shown in FIG. 5. Results show that the protein profile in the ECM can be modified by varying the ratios of native cells in the originating co-culture.

Figure 2:
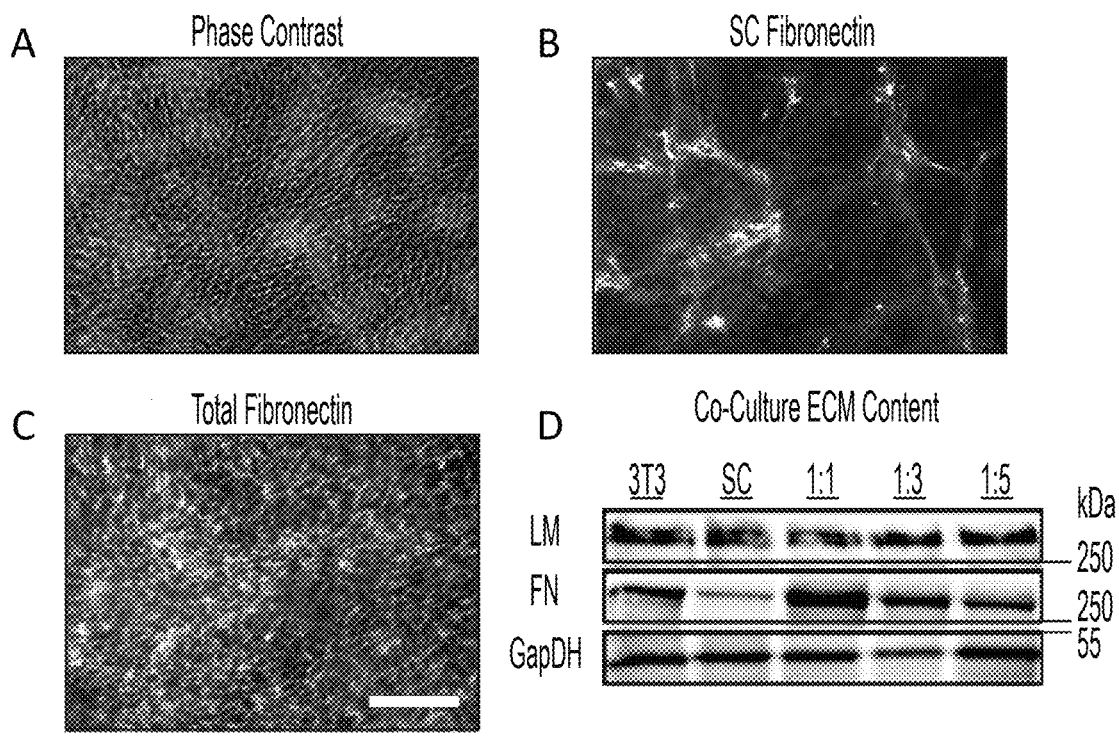
FIG. 2 is a series of microscopy images showing (A) co-culture of 3T3 fibroblasts and rat Schwann cells (SCs) with phase contrast, (B) co-culture of 3T3 fibroblasts and SCs imaged with labeled rat-specific monoclonal anti-fibronectin, (C) co-culture of 3T3 fibroblasts and SCs imaged with labeled total anti-fibronectin, and (D) a western blot showing fibronectin and laminin content for cell cultures of only 3T3s or SCs, and in co-culture ratios of 1:1, 1:3, and 1:5 (3T3 fibroblast:SC).

Example 2. Tissue-Specific ECM is Tunable to Provide a Desired Protein Composition Co-cultures of 3T3 fibroblasts and primary rat SCs (ratios set forth as 3T3:SC) were established in regenerative media (DMEM:F12+L-glutamine, 10% fetal bovine serum, 1% antibiotics, 10 ng/ml neuregulin, and 5 ng/ml TGFβ1). Decellularized ECM was obtained therefrom as previously described. Components of decellularized ECM were analyzed with immunostaining and Western blot using rat-specific anti-fibronectin, antibody to total fibronectin (detects total matrix assembly), and antibody to laminin, a prominent ECM component. FIGS. 2A-2C show microscopy images of co-cultures with phase contrast (FIG. 2A), rat-specific monoclonal anti-fibronectin (FIG. 2B), and total anti-fibronectin (FIG. 2C). Quantitation via Western blot (FIG. 2(D)) showed that the levels of these proteins fluctuated with the ratios of the fibroblasts, thereby demonstrating a tunable ECM that can be optimized for protein content using co-cultures of tissue-specific cells.

Example 3. Hybrid Polymer-ECM Composition for Electrospinning

ECM was prepared as described in Example 1. Pure ECM powder was thoroughly milled into a fine powder and added to 20% w/v PVDF-TrFE in (6:4) DMF-acetone solution for a final ECM concentration of approximately 0.05% to 0.1% w/v. This hybrid solution was mixed until the lyophilized ECM was sufficiently dissolved or dispersed solution. Electrospinning then proceeded according to established protocols, with sufficient attention paid to ensure the lyophilized particles did not aggregate within the syringe and impact deposition.

Briefly, nanofiber scaffolds were fabricated using an aligned electrospinning configuration (Fluidnatek LE-50). The hybrid solution was loaded into a syringe using a 20 gauge needle and ejected at a flow rate of 1 ml h$^{-1}$. The collector was placed 10 cm from the needle tip, wrapped with a conductive polymer liner (McMaster-Carr), and rotated at 2000 rpm to create aligned fibers. A voltage (15 kV) was applied to the needle tip while the rotating collector was grounded. The PVDF-TrFE-ECM solution was spun for about 2 hours to provide an electrospun nanofiber scaffold.

Example 4. Cell Proliferation and Alignment on Piezoelectric-ECM Nanofiber Scaffolds RT4-D6P2T Schwann cells (ATCC) and NIH 3T3 fibroblasts (ATCC) were cultured in high glucose Dulbecco's modified eagle medium (DMEM) (SH30022) (GE Healthcare) supplemented with either fetal bovine serum (10%) (Thermo Fisher) for Schwann cells or bovine calf serum (10%) (Thermo Fisher) for fibroblasts and pen/strep (1%) (Thermo Fisher) at 37° C. using CO2 (5%) and 95% relative humidity. Cells were grown to subconfluence before passaging via phosphate buffered saline (PBS) (Thermo Fisher) wash and dissociation by trypsin (0.25%) in versine (Gibco) solution.

PVDF-TrFE-ECM hybrid scaffolds were cut into approximately 2 cm×2 cm segments, placed on 18 mm diameter microscope coverslips (Fisher), and added to a 12-well plate. Coverslips were sterilized overnight under UV-light. Prior to cell seeding, polytetrafluoroethylene (PTFE) O-rings (ID, 10.8 mm; OD, 11.78 mm) (Wilmad Labglass) were placed upon the PVDF-TrFE-ECM segments to ensure polymers remain submerged after seeding. The scaffold segments were rinsed with ethanol (70%) and washed twice with PBS. Schwann cells and fibroblasts were then mixed with media and seeded at a final density of 75 000 cells $cm^{-1}$.

Postculture, PVDF-TrFE-ECM scaffolds were washed twice with PBS and fixed in formaldehyde (3.7%) for 15 min. Samples were washed twice with PBS and lysed with Triton X-100 (0.5%) for 5 min at 4° C. followed by two additional PBS washes. Samples were incubated in a dilution of 1:100 R457 primary antibody at 37° C. for 30 min and subsequently incubated in rhodamine-phalloidin (10 μg $mL^{-1}$) and Alexa Fluor 488 goat anti-mouse secondary antibody (1 μg $mL^{-1}$) at 37° C. for 30 min. Samples were then incubated in DAPI staining solution ($300 \times 10^{-9}$ m) at 37° C. for 5 min and then attached to glass microscope slides with mounting medium (50% glycerol, $20 \times 10^{-3}$ m Tris, 0.5% N-propyl gallate) and sealed with clear nail polish.

Wide-field images were captured with a Nikon Eclipse Ti2 inverted microscope and a Nikon DS-Qi2 camera using both fluorescent and phase microscopy. Confocal images were captured with a Nikon eclipse Ti inverted microscope on a Nikon AIR confocal using fluorescent microscopy.

For cell proliferation, Schwann cells and fibroblasts were seeded at a low density of 50 cells $mm^{-2}$ on 2 h spun aligned scaffolds and cultured for 24 and 72 h. Multiple experiments with three coverslips each were created for each experimental condition and 15 images per slide were captured using the DAPI channel in Nikon Elements software. For both the adhesion and proliferation assays, the "Object Count" feature of the Elements software was used to automatically calculate the total number of cells per image.

To analyze alignment, cells were cultured for 24 h under standard conditions on 2 h spun scaffolds before being fixed, immunolabeled, and imaged with either phase microscopy or confocal microscopy. Representative images of cell cultures on scaffolds were created by overlaying DAPI and TRITC channels.

Cell alignment was calculated using rhodamine-phalloidin staining in the NIH ImageJ software (version 1.52p) of cells on aligned and unaligned scaffolds, where representative images were processed using a Fast Fourier Transformation and subsequent oval profiles were quantified for radial sums from 0° to 180°. Full width at half-maximum values were then calculated from each respective radial sums curve. Two randomized images from each of the three coverslips were captured using Nikon NIS Elements software.

Statistical Analysis: data were reported as mean values±standard error. Statistical analysis was performed on excel and Origin 9.1. One-way analysis of variance (ANOVA) and Tukey's post-hoc test were used for comparative analysis and statistical significance, delineated as *, $p \leq 0.05$, $p \leq 0.005$, and *, $p \leq 0.0005$.

Figure 6:
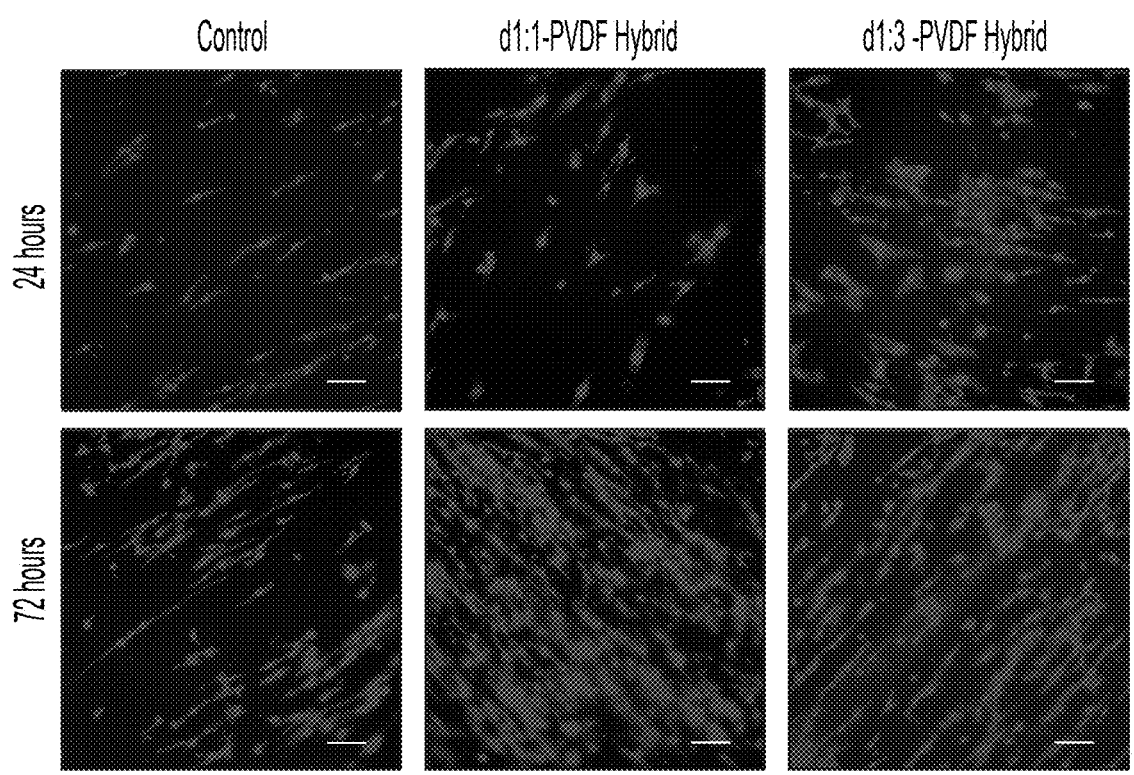
FIG. 6 is a series of images showing cellular attachment and proliferation to a control scaffold without ECM (first column), a piezoelectric scaffold electrospun with ECM obtained from a 1:1 co-culture ratio of 3T3:SC (second column), and a piezoelectric scaffold electrospun with ECM obtained from a 1:3 co-culture ratio 3T3:SC (third column) at 24 hours (top row) and 72 hours (bottom row).
Figure 7:
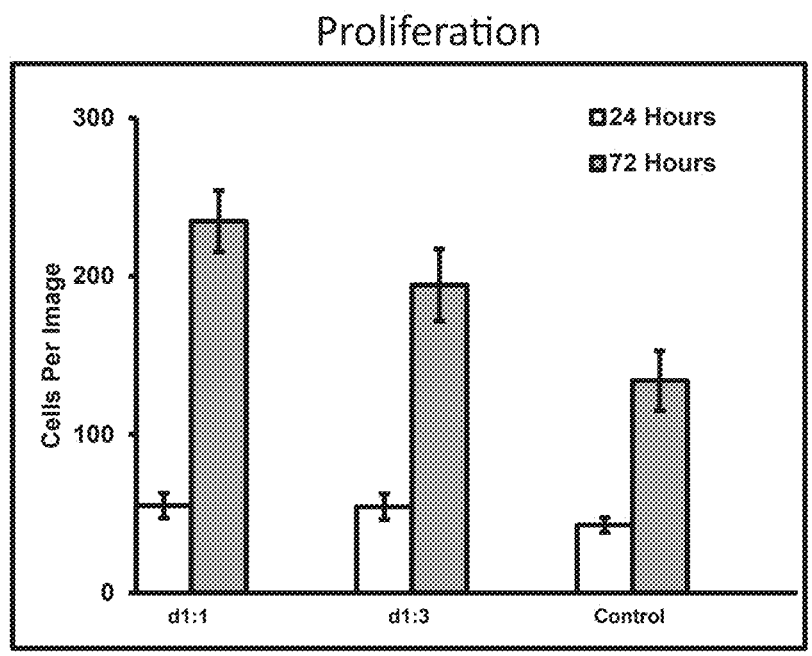
FIG. 7 is a graph showing cellular proliferation at 24 hours and 72 hours for control scaffold vs. scaffolds electrospun with ECM isolated from co-cultures of different ratios of 3T3:SC.

As shown in FIGS. 6 and 7, cells grown on scaffolds containing decellularized ECM in a 1:1 fibroblast:SC and 1:3 fibroblast:SC ratio (d1:1 and d1:3) show higher proliferation rates than cells without ECM (control), as evidenced by staining for cytoskeletal and DNA proteins over 72 hours. The 1:1 ratio showed highest amounts of cell proliferation across all conditions over a 72 hour period.

Figure 8:
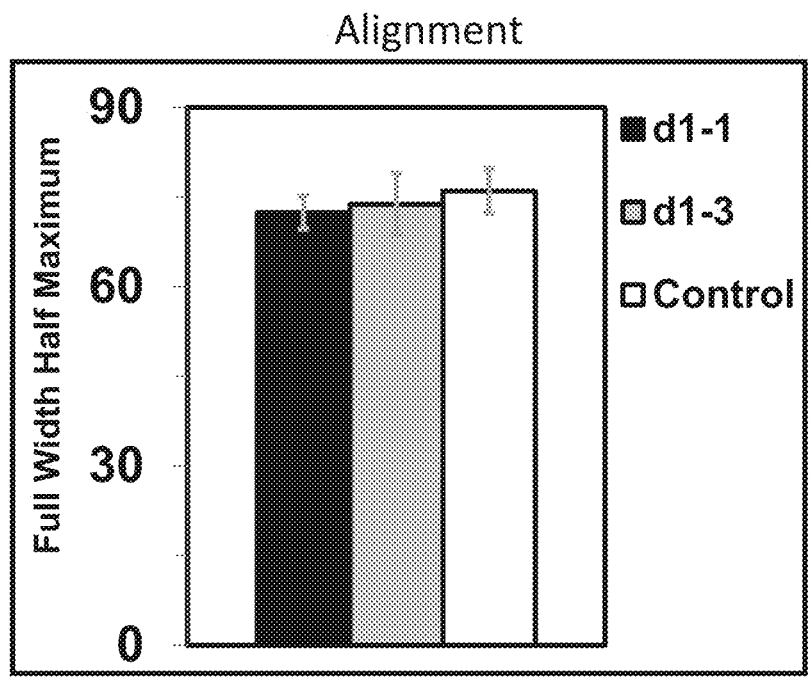
FIG. 8 is a graph showing alignment of attached cells for control scaffold vs. scaffolds electrospun with ECM isolated from co-cultures of different ratios of 3T3:SC.

Quantification of cell numbers over 72 hours show a significant increase in viable cells in the scaffold with ECM over the scaffold without ECM. FIG. 8 shows that alignment of cells is retained in the scaffolds with ECM and is not lost from controls. A high degree of alignment is important in tissue structure, which can be controlled with the ECM scaffolds.

Example 5. Ultrasound Stimulation of a Piezoelectric-ECM Nanofiber Scaffold

Ultrasound stimulation may be applied to selectively stimulate the disclosed biomaterials in an in vivo environment. In order to evaluate this method, a sample of the piezoelectric scaffold is floated in approximately 20 mL of deionized water with unsubmerged electrodes on either end of the scaffold. Ultrasound stimulation with a frequency of 20 kHz and a maximum power of 125 W is applied to the scaffold in one-second pulses for a maximum of five cycles, ensuring that the sample does not overheat. The resulting current is measured by a picoammeter. Results show that low intensity ultrasound stimulates the piezoelectric scaffold to generate a charge, as measured by the electrodes. Results indicate that low intensity ultrasound is a viable method for targeted stimulation of a piezoelectric scaffold in vivo. Further, it has previously been shown that low intensity ultrasound has a positive effect on cellular proliferation and metabolic activity.

Embodiments can be described with reference to the following numbered clauses, with preferred features laid out in dependent clauses.

1. An implantable biomaterial for promoting regeneration of a biological tissue, the biomaterial comprising: a piezoelectric material; and an extracellular matrix specific to the injured biological tissue, wherein the piezoelectric material and the extracellular matrix are electrospun together to provide a tissue-specific bioactive piezoelectric nanofiber scaffold.

2. The biomaterial according to clause 1, wherein the piezoelectric material is selected from the group consisting of polyvinylidene fluoride-trifluoroethylene (PVDF-TrFE), barium titanate (BT), sodium potassium niobate (KNN), boron nitride (BN), zinc oxide (ZnO), poly-L-lactic acid (PLLA), PVDF copolymers, polyhydroxybutyrate (PHB) copolymers, polylactic acid (PLA), collagen, and combinations thereof.

3. The biomaterial according to any of the preceding clauses, wherein the electrospun piezoelectric nanofibers are substantially uniaxially aligned.

4. The biomaterial according to any of the preceding clauses, wherein the extracellular matrix is derived from cells native to a microenvironment of the biological tissue.

5. The biomaterial according to any of the preceding clauses, wherein the biological tissue is selected from the group consisting of nerve, bone, skin, cartilage, tendons, ligaments, muscle, heart, and combinations thereof.

6. The biomaterial according to any of the preceding clauses, wherein the biological tissue comprises peripheral nerve tissue and the extracellular matrix is derived from a co-culture of Schwann cells and fibroblasts.

7. A method for fabricating a biomaterial for regeneration of a biological tissue, the method comprising: electrospinning a piezoelectric material together with an extracellular matrix specific to the injured biological tissue to provide a tissue-specific bioactive piezoelectric nanofiber scaffold.

8. The method according to clause 7, wherein the piezoelectric material is selected from the group consisting of polyvinylidene fluoride-trifluoroethylene (PVDF-TrFE), barium titanate (BT), sodium potassium niobate (KNN), boron nitride (BN), zinc oxide (ZnO), poly-L-lactic acid (PLLA), PVDF copolymers, polyhydroxybutyrate (PHB) copolymers, polylactic acid (PLA), collagen, and combinations thereof.

9. The method according to any of clauses 7-8, wherein the electrospun piezoelectric nanofibers are substantially uniaxially aligned.

10. The method according to any of clauses 7-9, wherein the biological tissue is selected from the group consisting of nerve, bone, skin, cartilage, tendons, ligaments, muscle, heart, and combinations thereof.

11. The method according to any of clauses 7-10, wherein the extracellular matrix is derived from a co-culture of cells native to a microenvironment of the injured biological tissue.

12. The method according to any of clauses 7-11, wherein the biological tissue comprises peripheral nerve tissue and the extracellular matrix is derived from a co-culture of Schwann cells and fibroblasts.

13. The method according to any of clauses 7-12, wherein a ratio fibroblasts to Schwann cells in the co-culture ranges from about 1:1 to about 1:5.

14. A method of promoting regeneration of injured biological tissue in a patient in need thereof, the method comprising: providing a tissue-specific bioactive piezoelectric nanofiber scaffold comprising a piezoelectric material and an extracellular matrix specific to the injured biological tissue of the patient, wherein the piezoelectric material and the extracellular matrix are electrospun together to form nanofibers; and implanting the tissue-specific bioactive piezoelectric nanofiber scaffold at the site of the injured biological tissue of the patient, wherein the tissue-specific bioactive piezoelectric nanofiber scaffold delivers one or more stimuli to the site of the injured biological tissue that promote regeneration of the injured biological tissue.

15. The method according to clause 14, wherein the one or more stimuli are selected from the group consisting of an electrical stimulus, a physical stimulus, and a chemical stimulus.

16. The method according to any of clauses 14-15, wherein the piezoelectric material is selected from the group consisting of polyvinylidene fluoride-trifluoroethylene (PVDF-TrFE), barium titanate (BT), sodium potassium niobate (KNN), boron nitride (BN), zinc oxide (ZnO), poly-L-lactic acid (PLLA), PVDF copolymers, polyhydroxybutyrate (PHB) copolymers, polylactic acid (PLA), collagen, and combinations thereof.

17. The method according to any of clauses 14-16, wherein the electrospun nanofibers are substantially uniaxially aligned.

18. The method according to any of clauses 14-17, wherein the extracellular matrix is derived from a co-culture of cells native to a microenvironment of the injured biological tissue.

19. The method according to any of clauses 14-18, wherein the injured biological tissue is selected from the group consisting of nerve, bone, skin, cartilage, tendons, ligaments, muscle, heart, and combinations thereof.

20. The method according to any of clauses 14-19, wherein the injured biological tissue comprises peripheral nerve tissue and the extracellular matrix is derived from a co-culture of Schwann cells and fibroblasts.

21. The method according to clause 18, wherein the cells native to the microenvironment of the injured biological tissue are allogeneic or autologous to the patient.

22. The method according to any of clauses 14-21, further comprising applying ultrasound stimulation locally to an implantation region of the patient to selectively stimulate the bioactive piezoelectric nanofiber scaffold implanted in the patient.

23. The method according to clause 22, wherein the ultrasound stimulation comprises minimally-invasive low intensity ultrasound stimulation.

All documents cited are incorporated herein by reference; the citation of any document is not to be construed as an admission that it is prior art with respect to the present invention.

It is to be further understood that where descriptions of various embodiments use the term "comprising," and/or "including" those skilled in the art would understand that in some specific instances, an embodiment can be alternatively described using language "consisting essentially of" or "consisting of."

The foregoing description is illustrative of particular embodiments of the invention but is not meant to be a limitation upon the practice thereof. While particular embodiments have been illustrated and described, it would be obvious to one skilled in the art that various other changes and modifications can be made without departing from the spirit and scope of the invention. It is therefore intended to cover in the appended claims all such changes and modifications that are within the scope of this invention.

We claim:

1. An implantable biomaterial for promoting regeneration of an injured biological tissue, the biomaterial comprising:
   a piezoelectric material comprising a polyvinylidene fluoride (PVDF) copolymer; and
   a decellularized extracellular matrix specific to the injured biological tissue,
   wherein the piezoelectric material and the decellularized extracellular matrix are electrospun together to provide a tissue-specific bioactive piezoelectric nanofiber scaffold, and
   wherein the electrospun piezoelectric nanofibers of the scaffold are substantially uniaxially aligned.

2. The biomaterial according to claim 1, wherein the piezoelectric material comprises polyvinylidene fluoride-trifluoroethylene (PVDF-TrFE).

3. The biomaterial according to claim 1, wherein the decellularized extracellular matrix is derived from cells native to a microenvironment of the injured biological tissue.

4. The biomaterial according to claim 3, wherein the injured biological tissue is selected from the group consisting of nerve, bone, skin, cartilage, tendons, ligaments, muscle, heart, and combinations thereof.

5. The biomaterial according to claim 4, wherein the injured biological tissue comprises peripheral nerve tissue and wherein the cells native to the microenvironment of the injured biological tissue are a co-culture of Schwann cells and fibroblasts.

6. The biomaterial according to claim 1, wherein the piezoelectric material further comprises one or more of barium titanate (BT), sodium potassium niobate (KNN), boron nitride (BN), zinc oxide (ZnO), poly-L-lactic acid (PLLA), polyhydroxybutyrate (PHB) copolymers, and polylactic acid (PLA).

7. A method for fabricating a biomaterial for regeneration of an injured biological tissue, the method comprising:
   providing a hybrid solution comprising:
     a piezoelectric material comprising a polyvinylidene fluoride (PVDF) copolymer;
     and a decellularized extracellular matrix specific to the injured biological tissue;

electrospinning the hybrid solution to provide a tissue-specific bioactive piezoelectric nanofiber scaffold, wherein the electrospun piezoelectric nanofibers of the scaffold are substantially uniaxially aligned.

8. The method according to claim 7, wherein the piezoelectric material comprises polyvinylidene fluoride-trifluoroethylene (PVDF-TrFE).

9. The method according to claim 7, wherein the injured biological tissue is selected from the group consisting of nerve, bone, skin, cartilage, tendons, ligaments, muscle, heart, and combinations thereof.

10. The method according to claim 9, wherein the decellularized extracellular matrix is derived from a co-culture of cells native to a microenvironment of the injured biological tissue.

11. The method according to claim 10, wherein the injured biological tissue comprises peripheral nerve tissue and wherein the co-culture of cells native to the microenvironment of the injured biological tissue is a co-culture of Schwann cells and fibroblasts.

12. The method according to claim 11, wherein a ratio of fibroblasts to Schwann cells in the co-culture ranges from about 1:1 to about 1:5.

13. The method according to claim 7, wherein the piezoelectric material further comprises one or more of barium titanate (BT), sodium potassium niobate (KNN), boron nitride (BN), zinc oxide (ZnO), poly-L-lactic acid (PLLA), polyhydroxybutyrate (PHB) copolymers, and polylactic acid (PLA).

14. A method of promoting regeneration of injured biological tissue in a patient in need thereof, the method comprising:

providing a tissue-specific bioactive piezoelectric nanofiber scaffold comprising a piezoelectric material comprising a polyvinylidene fluoride (PVDF) copolymer and a decellularized extracellular matrix specific to the injured biological tissue of the patient, wherein the piezoelectric material and the decellularized extracellular matrix are electrospun together to form substantially uniaxially aligned nanofibers; and implanting the tissue-specific bioactive piezoelectric nanofiber scaffold at a site of the injured biological tissue of the patient, wherein the tissue-specific bioactive piezoelectric nanofiber scaffold delivers one or more stimuli to the site of the injured biological tissue that promote regeneration of the injured biological tissue.

15. The method according to claim 14, wherein the one or more stimuli are selected from the group consisting of an electrical stimulus, a physical stimulus, and a chemical stimulus.

16. The method according to claim 14, wherein the piezoelectric material comprises polyvinylidene fluoride-trifluoroethylene (PVDF-TrFE).

17. The method according to claim 14, wherein the decellularized extracellular matrix is derived from a co-culture of cells native to a microenvironment of the injured biological tissue.

18. The method according to claim 17, wherein the injured biological tissue is selected from the group consisting of nerve, bone, skin, cartilage, tendons, ligaments, muscle, heart, and combinations thereof.

19. The method according to claim 18, wherein the injured biological tissue comprises peripheral nerve tissue and wherein the co-culture of cells native to the microenvironment of the injured biological tissue is a co-culture of Schwann cells and fibroblasts.

20. The method according to claim 17, wherein the cells native to the microenvironment of the injured biological tissue are allogeneic or autologous to the patient.

21. The method according to claim 14, further comprising applying ultrasound stimulation locally to an implantation region of the patient to selectively stimulate the bioactive piezoelectric nanofiber scaffold implanted in the patient.

22. The method according to claim 21, wherein the ultrasound stimulation comprises minimally-invasive low intensity ultrasound stimulation.

23. The method according to claim 14, wherein the piezoelectric material further comprises one or more of barium titanate (BT), sodium potassium niobate (KNN), boron nitride (BN), zinc oxide (ZnO), poly-L-lactic acid (PLLA), polyhydroxybutyrate (PHB) copolymers, and polylactic acid (PLA).

* * * * *